US00PP24259P3

(12) United States Plant Patent
Probasco et al.

(10) Patent No.: US PP24,259 P3
(45) Date of Patent: Feb. 25, 2014

(54) HOT PLANT NAMED 'HBC 342'

(50) Latin Name: *Humulus lupulus*
Varietal Denomination: HBC 342

(76) Inventors: Eugene G. Probasco, Yakima, WA (US); Jason Perrault, Toppenish, WA (US)

( * ) Notice: Subject to any disclaimer, the term of this patent is extended or adjusted under 35 U.S.C. 154(b) by 0 days.

(21) Appl. No.: 12/932,776

(22) Filed: Mar. 4, 2011

(65) Prior Publication Data

US 2011/0225686 P1 Sep. 15, 2011

Related U.S. Application Data

(60) Provisional application No. 61/339,848, filed on Mar. 9, 2010.

(51) Int. Cl.
*A01H 5/00* (2006.01)

(52) U.S. Cl.
USPC ..... Plt./236

(58) Field of Classification Search
USPC ..... Plt./236
See application file for complete search history.

*Primary Examiner* — Kent L Bell
(74) *Attorney, Agent, or Firm* — Ballew Law

(57) ABSTRACT

A new hop plant named 'HBC 342' is disclosed. The cones of 'HBC 342' mature in late September to early October, and yield a crop of 2400 to 3000 pounds per acre. 'HBC 342' is used for its late maturity, high alpha acid content and exceptional yield.

6 Drawing Sheets

Genus and species: *Humulus lupulus.*
Variety denomination: 'HBC 342'.

STATEMENT REGARDING FEDERALLY SPONSORED RESEARCH OR DEVELOPMENT

None

BACKGROUND OF THE INVENTION

'HBC 342' is a product of a controlled breeding program carried out by the inventors in the Yakima Valley of Washington state. 'HBC 342' was one of several seedlings resulting from a cross made in 2001 of female parent 'YCR 45' (not patented) and male parent '97M2' (not patented). A single plant of 'HBC 342' was selected in 2004, and was expanded to 70 plants, which were then planted in the area of Toppenish, Wash. The plants were observed and evaluated for several years, and in 2009 were expanded for further observation and evaluation in the Toppenish, Washington area. A 40 acre test plot of 'HBC 342' was established in 2009. Throughout several generations of asexual propagation by softwood cuttings at a greenhouse facility in Yakima, Wash., 'HBC 342' has been observed to retain its distinctive characteristics and remain true to type.

COMPARISON WITH OTHER VARIETIES

COMPARISON OF THE ACCESSION

| | HBC 342 | YCR 45 (Maternal parent) | Nugget (comp variety) |
|---|---|---|---|
| Species: | *H. lupulus* | *H. lupulus* | *H. lupulus* |
| Ploidy: | 2n = 2x | 2n = 2x | 2n = 2x |
| Sex: | Female | Female | Female |

-continued

COMPARISON OF THE ACCESSION

| | HBC 342 | YCR 45 (Maternal parent) | Nugget (comp variety) |
|---|---|---|---|
| Use: | Beer bittering/ flavor | Experimental | Brewing beer |
| Powdery Mildew: | resistant | resistant | resistant |
| Downy Mildew: | susceptible | susceptible | susceptible |
| Verticillium Wilt: | NA | NA | NA |
| Cone: | medium size, dense | medium size, dense | medium size, medium dense |
| Pickability: | good | good | good |
| Maturity: | September 25-October 7 | September 15-September 25 | September 10-September 20 |
| Yield (lb per acre): | 2400-3000 | | 1800-2200 |
| % alpha acids (% of cone weight): | 12.4-15.2 | 8.5-11.5 | 11.5-14.0 |
| % beta acids (% of cone weight): | 4.7-5.7 | 8.5-11.5 | 4.2-5.8 |
| % cohumulone (% of alpha acids): | 34.0-36.9 | 53-55 | 22-26 |
| Total oils (ml/100 g of cones): | 1.0 | 1.3-2.3 | 1.8-2.2 |
| Storageability (% alpha remaining, 6 mo. room temp): | 70-80 | 60-70 | 70-80 |
| Aroma profile: | mild-fruity, watermelon, citrus | na | mild/herbal |

BRIEF DESCRIPTION OF THE PHOTOGRAPHS

Figure 1:
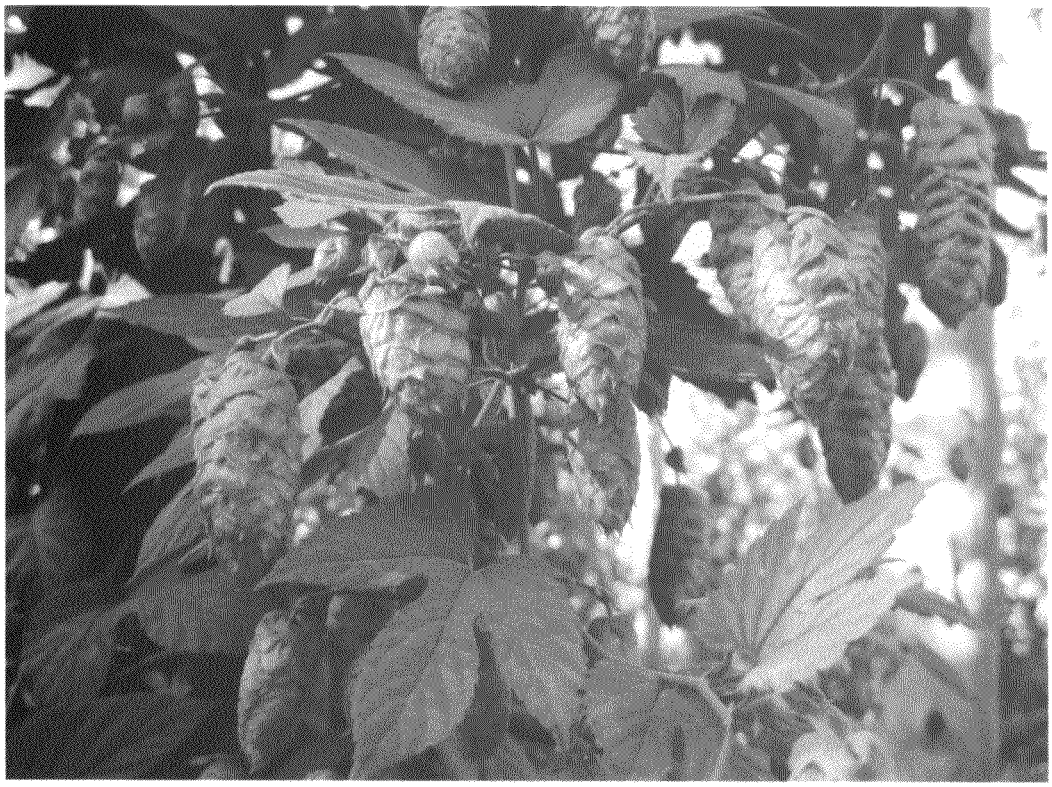
Figure 2:
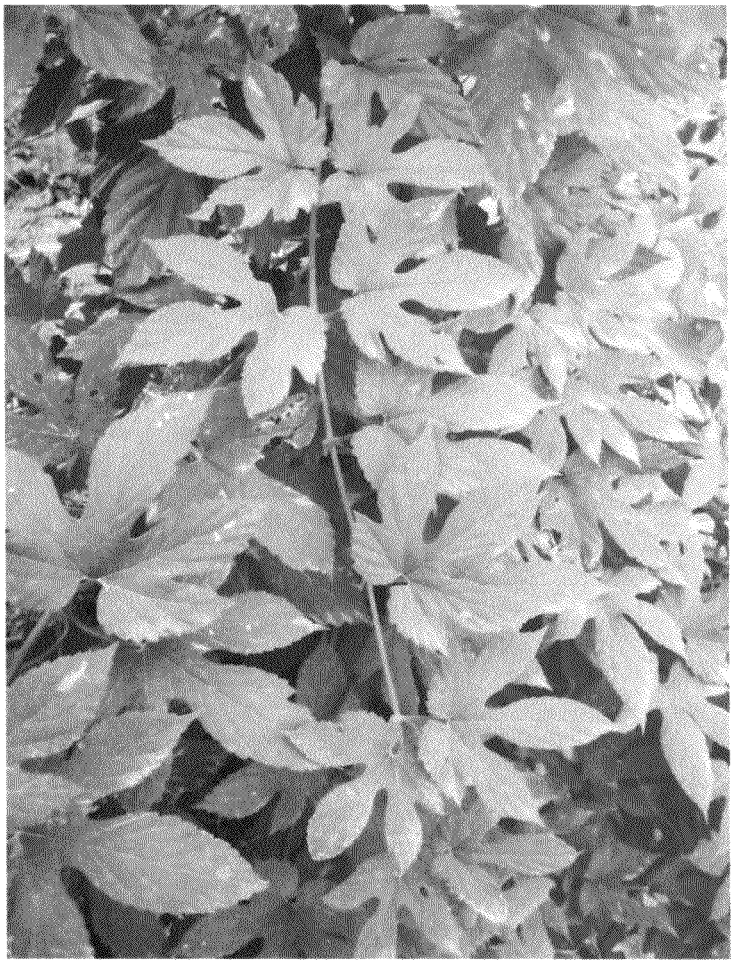
Figure 3:
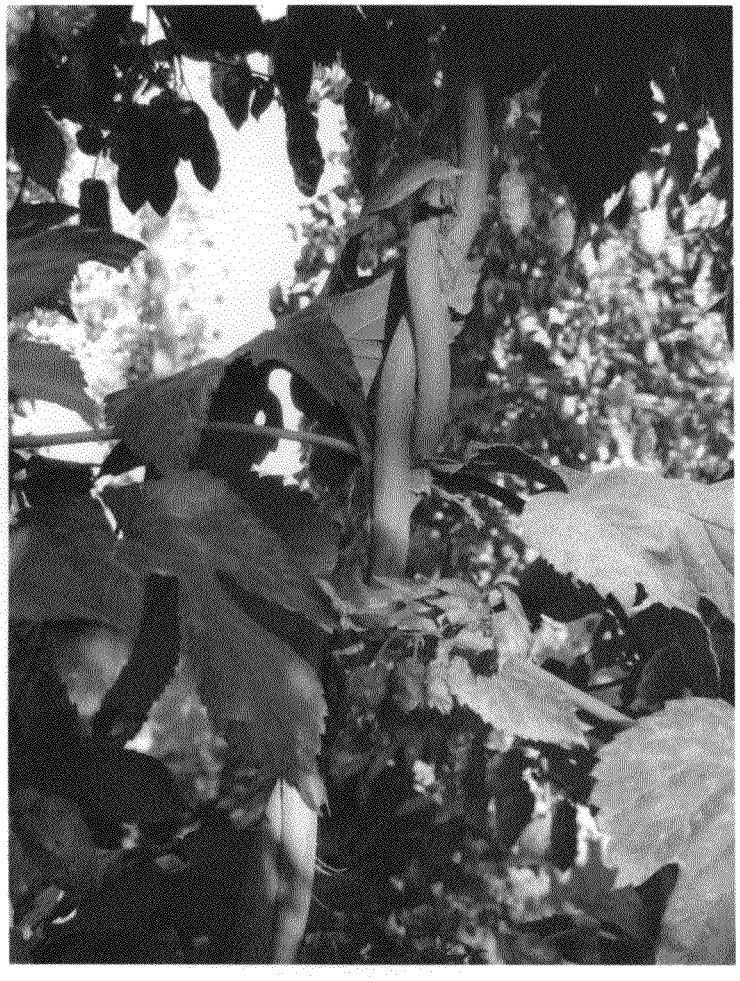
Figure 4:
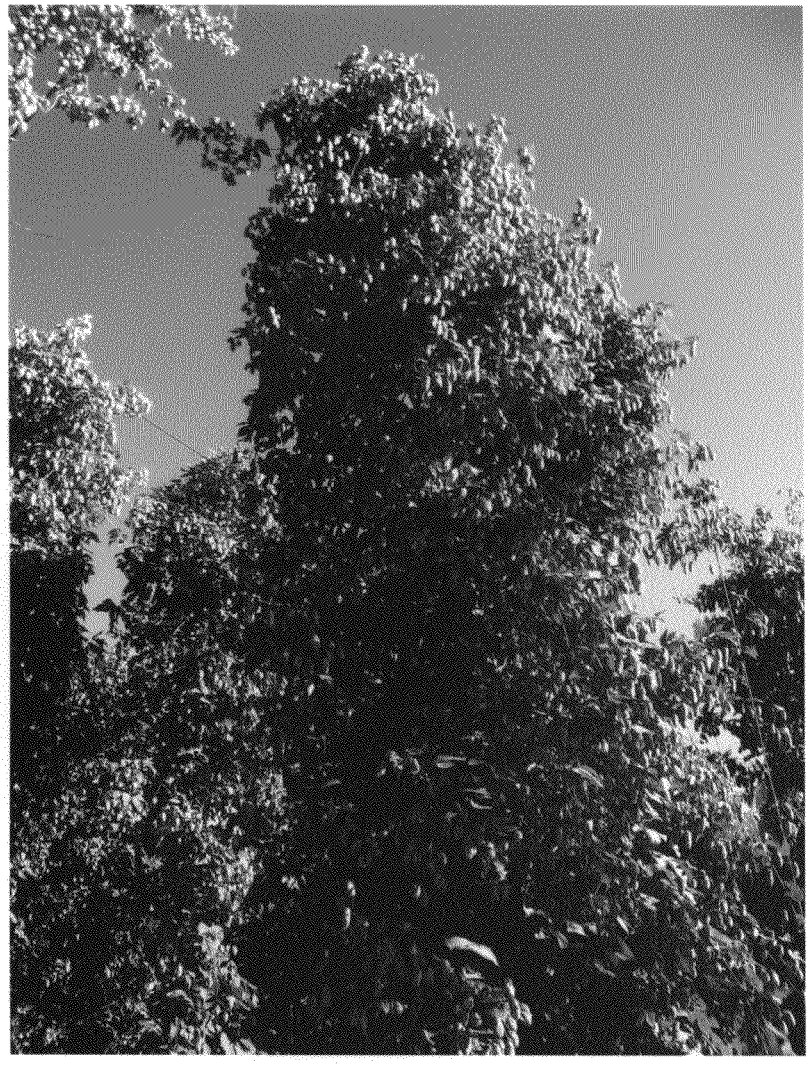
Figure 5:
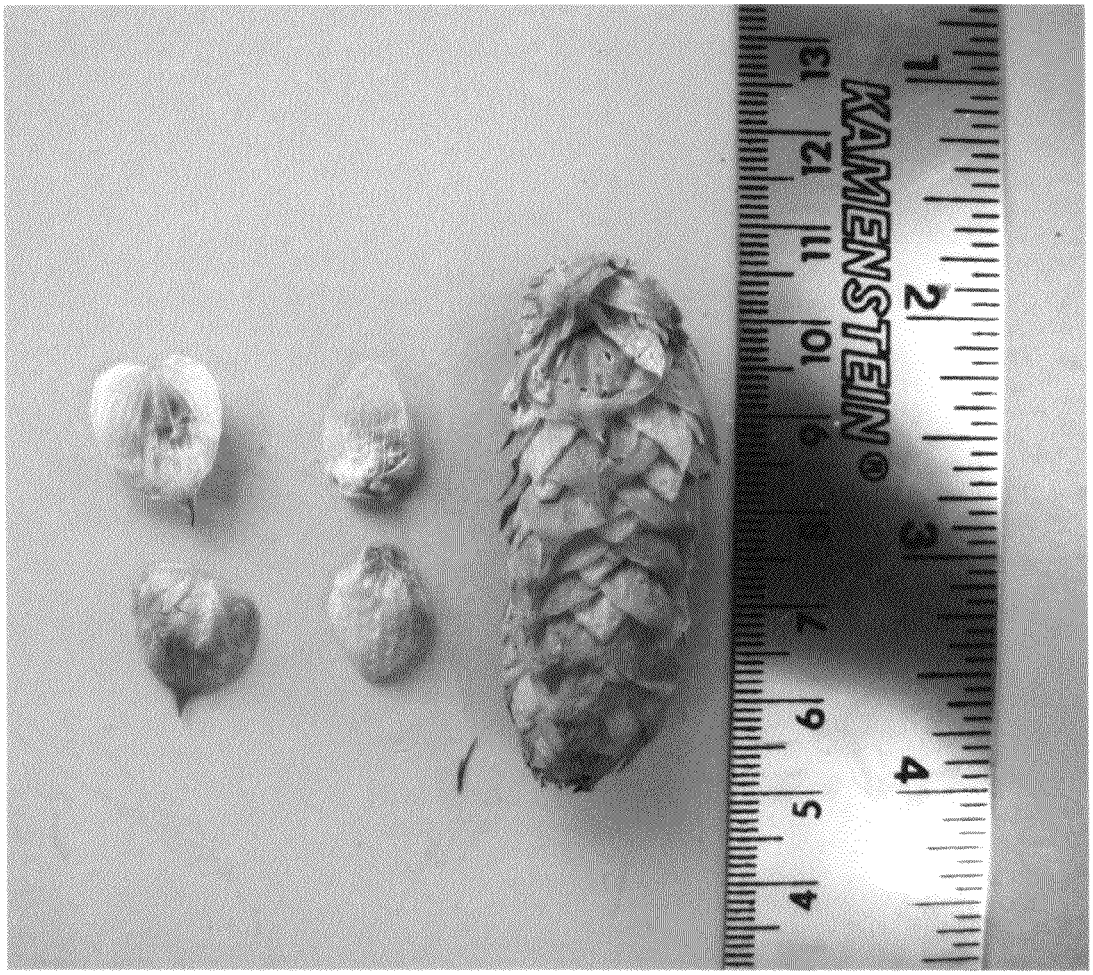
Figure 6:
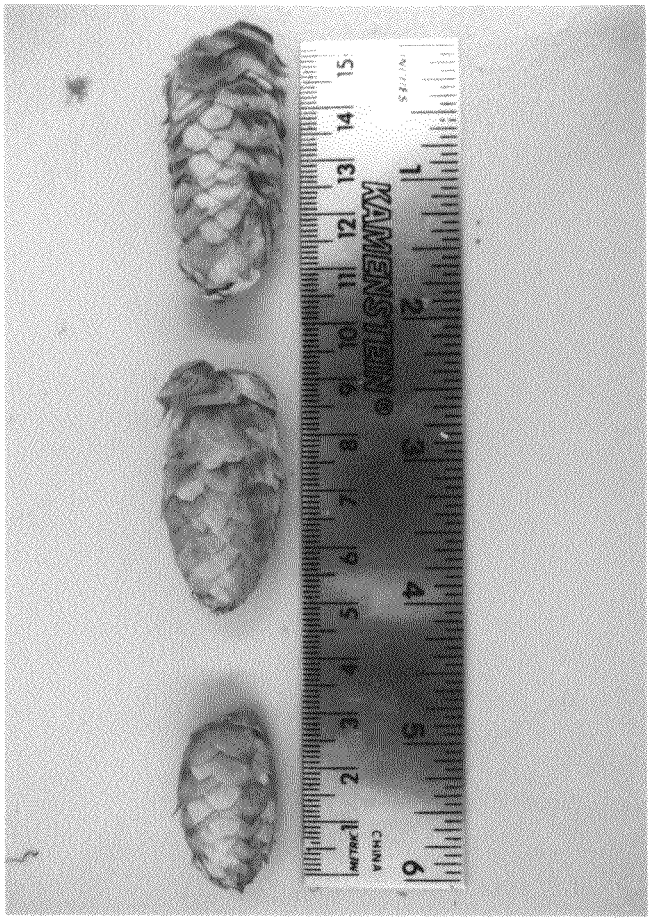

FIG. 1 illustrates cones of the 'HBC 342' hop plant;
FIG. 2 illustrates leaves of the 'HBC 342' hop plant;
FIG. 3 illustrates the bine and leaves of the 'HBC 342' hop plant;
FIG. 4 illustrates a mature 'HBC 342' hop plant grown on a trellis;
FIG. 5 illustrates a cone, bract and bracteole of the 'HBC 342' hop plant; and
FIG. 6 illustrates cones, of the 'HBC 342' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2010 growing season at Toppenish, Wash. Color descriptions refer to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Species: *Humulus lupulus*.
Ploidy: Diploid.
Use: Brewing.
Disease susceptibility: 'HBC 342' is not resistant to mild infestations of hop downy mildew. 'HBC 342' is resistant to powdery mildew.
Pest susceptibility: 'HBC 342' is not resistant to normal infestations of hop aphid and two-spotted spider mite.
Crop yield: 2400-3000 pounds per acre.
Harvest date: September 25-October 7.
Plant shape: Columnar.
Bine:
- *Color*.—Yellow green 145A, stripe present — Grayed Purple N186C.
- *Stipule direction*.—Down-forked.
- *Stipule color*.—Yellow green 144A.
- *Bine diameter*.—10.0 mm at base; 9.0 mm at 9 feet; 8.0 mm at 18 feet.
- *Bine length*.—5.5 —7.0 m.
- *Bine internode length*.—24.5 cm.

Lateral:
- *Color*.—Yellow green 146D.
- *Lateral length*.—90.9 cm.
- *Lateral internode length*.—11.3 cm.
- *Lateral diameter*.—4 mm.

Leaf:
- *Arrangement*.—Opposite.
- *Shape*.—Cordate; Palmate lobes.
- *Leaf base shape*.—Cordate.
- *Leaf apex shape*.—Acuminate, acute.
- *Average length of mature leaf*.—16.3 cm.
- *Average width of mature leaf*.—16 cm.
- *Color of mature leaf upper surface*.—Yellow green 147A.
- *Color of mature leaf lower surface*.—Yellow green 146A.
- *Color of immature leaf upper surface*.—Green 137B.
- *Color of immature leaf lower surface*.—Green 138B.
- *Number of lobes*.—3-7.
- *Margin*.—Serrate.
- *Serrations per inch*.—5-12.
- *Average petiole length* (*mature*).—8.2 cm.
- *Petiole color*.—Yellow green146D.
- *Petiole color at base*.—Yellow green N186C.
- *Petiole diameter*.—3 mm.
- *Venation*.—Palmate.
- *Vein color*.—Yellow green 145B.

Cone:
- *Average length*.—4.5 cm.
- *Average diameter*.—1.9 cm.
- *Average weight*.—1132 mg.
- *Bract tip color*.—Yellow green 144A.
- *Bract base color*.—Yellow green 149D.
- *Bract length*.—15 mm.
- *Bract width*.—12 mm.
- *Bracteole color*.—Yellow green 149D.
- *Bracteole length*.—13 mm.
- *Bracteole width*.—8 mm.
- *Cone shape*.—Ovoid.
- *Bract shape*.—Ovate.
- *Bract tip shape*.—Mucronate.
- *Bract tip position*.—Loosely appressed.
- *Bracteole shape*.—Ovate.
- *Lupulin glands*.—While not particularly distinctive, Shape — globular; Quantity — numerous; Color — yellow 2A.
- *Pickability*.—Fair.

Qualitative analysis:
- *Alpha acids* (*as % of cone weight*).—12.0% to 15.0%.
- *Beta acids* (*as % of cone weight*).—4.5% to 5.5%.
- *Cohumulone* (*as % of alpha acids*).—34.0% to 37.0%.
- *Myrcene* (*as % of total oils*).—41.0% to 57.0%.
- *Humulene* (*as % of total oils*).—9.5% to 13.0%.
- *Caryophyllene* (*as % of total oils*).—8.0% to 10.5%.
- *Total oils*.—1.0 to 1.5 ml per 100 g cones.
- *Storageability*.—70% to 80% alpha acids remaining after 6 months storage at room temperature.

It is claimed:

1. A new and distinct hop plant as shown and described herein.

* * * * *